US005906957A

United States Patent [19]

Benazzi et al.

[11] Patent Number: 5,906,957

[45] Date of Patent: May 25, 1999

[54] SOLID ALIPHATIC ALKYLATION CATALYST

[75] Inventors: Eric Benazzi, Montesson; Jean-Francois Joly, Lyons, both of France

[73] Assignee: Institut Francais du Petrole, France

[21] Appl. No.: 08/711,151

[22] Filed: Sep. 10, 1996

[30] Foreign Application Priority Data

Sep. 11, 1995 [FR] France .................................. 95 10695

[51] Int. Cl.[6] ............................ B01J 27/02; B01J 27/06; B01J 21/08; C07C 2/58

[52] U.S. Cl. .......................... 502/216; 502/224; 502/232; 502/300; 585/709; 585/721; 585/730; 585/732

[58] Field of Search .................................... 502/216, 224, 502/232, 300; 585/709, 721, 730, 732

[56] References Cited

U.S. PATENT DOCUMENTS

| | | | |
|---|---|---|---|
| 3,795,712 | 3/1974 | Torck et al. | 260/671 C |
| 4,008,178 | 2/1977 | Brockington | 502/217 |
| 4,022,847 | 5/1977 | McClure | 585/747 |
| 4,056,578 | 11/1977 | McClure et al. | 585/730 |
| 4,060,565 | 11/1977 | McClure et al. | 585/462 |
| 4,118,433 | 10/1978 | Innes | 585/728 |
| 5,196,628 | 3/1993 | Del Rossi et al. | 585/725 C |
| 5,336,833 | 8/1994 | Joly et al. | 585/731 |
| 5,349,116 | 9/1994 | Kallenbach et al. | 585/730 |
| 5,420,093 | 5/1995 | Joly et al. | 502/216 |
| 5,444,175 | 8/1995 | Joly et al. | 585/731 |
| 5,475,184 | 12/1995 | Joly et al. | 585/731 |
| 5,489,560 | 2/1996 | Joly et al. | 585/731 |
| 5,489,728 | 2/1996 | Benazzi et al. | 585/731 |
| 5,607,890 | 3/1997 | Chen et al. | 502/221 |

FOREIGN PATENT DOCUMENTS

| | | | |
|---|---|---|---|
| 0 605 279 | 7/1994 | European Pat. Off. | B01J 31/02 |
| 0 623 388 | 11/1994 | European Pat. Off. | B01J 31/02 |
| 93/00316 | 1/1993 | WIPO | C07C 2/58 |

*Primary Examiner*—Mark L. Bell
*Assistant Examiner*—Patricia L. Hailey
*Attorney, Agent, or Firm*—Millen, White, Zelano & Branigan, P.C.

[57] ABSTRACT

The invention concerns a catalyst comprising a porous organic or inorganic support and at least one active phase comprising at least one acid selected from acids with formula R—$SO_3H$, where R is fluorine or an alkyl group or a fluorinated alkyl group, and at least one weakly basic aprotic organic solvent, the support having been impregnated with the active phase, the catalyst being such that it is essentially constituted by particles with an average diameter in the range 0.1 $\mu$m to 150 $\mu$m, and being such that before impregnation with the active phase, the support has a total pore volume in the range 0.5 $cm^3/g$ to 6 $cm^3/g$. The invention also concerns the use of the catalyst for aliphatic alkylation.

22 Claims, No Drawings

SOLID ALIPHATIC ALKYLATION CATALYST

FIELD OF THE INVENTION

The present invention concerns a catalyst comprising a porous organic or inorganic support and at least one active phase comprising at least one acid selected from acids with formula R—$SO_3$H, where R is fluorine or an alkyl group or a fluorinated alkyl group (partially or completely fluorinated), R preferably being F or $CF_3$, and more preferably $CF_3$, and at least one weakly basic aprotic organic solvent. The invention also concerns the use of the catalyst for aliphatic alkylation, i.e., catalytic alkylation of isobutane and/or isopentane using at least one olefin containing 3 to 6 carbon atoms per molecule (i.e., a $C_3$–$C_6$ olefin), to obtain paraffinic compounds with a high degree of branching and a high octane number.

BACKGROUND OF THE INVENTION

A large number of liquid or solid acid catalysts are known for use in carrying out the aliphatic alkylation of isoparaffin(s) such as isobutane or isopentane using at least one olefin such as propylene, 1- and 2-butenes or isobutene. The catalysts which are most frequently used in the industry are liquid catalysts, namely concentrated sulphuric acid and hydrofluoric acid, used alone or mixed with Lewis acids such as boron trifluoride. These processes suffer considerable disadvantages: hydrofluoric acid because of its toxicity and high volatility; and sulphuric acid because of its high consumption of catalyst, necessitating costly reprocessing. For this reason, the use of solid catalyst or catalyst supported on solids such as aluminosilicates or metallic oxides, for example zirconia treated with sulphuric acid, has been recommended.

In order to catalyse the alkylation of aromatic compounds by at least one olefin or the aliphatic alkylation of isobutane by at least one olefin or the oligomerisation or polymerisation of olefins, U.S. Pat. No. 3,795,712 describes catalytic compositions comprising a Lewis or Brönsted acid and a sulphone with formula R—$SO_2$—R', where R and R' are each and separately a monovalent radical comprising 1 to 8 carbon atoms per molecule, or together form a divalent radical containing 3 to 12 carbon atoms per molecule, optionally in an inert hydrocarbon solvent. The acid concentration is in the range $10^{-5}$ moles per litre of sulphone to 5 moles per litre of sulphone, i.e., in the range 0.00012% to 37% by weight of acid when the acid is trifluoromethanesulphonic acid and the sulphone is sulpholane.

International patent application PCT WO 93/00316 describes catalytic compositions for aliphatic alkylation comprising 10% to 90% by weight of hydrofluoric acid or sulphonic acid substituted with at least one halogen and 10% to 90% by weight of a solvent with a donor number of less than 40 in the absence of a deliberate addition of a metal halide. The long list of such solvents includes sulpholane (tetramethylene sulphone) and dimethylsulphoxide.

SUMMARY OF THE INVENTION

The catalyst of the present invention constitutes an improvement over the catalytic compositions described in U.S. Pat. No. 3,795,712 and WO 93/00316 used for aliphatic alkylation.

The present invention concerns a catalyst comprising a porous organic or inorganic support and at least one active phase comprising at least one acid selected from acids with formula R—$SO_3$H, where R is fluorine or an alkyl group or a fluorinated alkyl group (partially or completely fluorinated), R preferably being F or $CF_3$, more preferably $CF_3$, and at least one weakly basic aprotic organic solvent, the support having been impregnated with the active phase, the catalyst being such that it is essentially constituted by particles with an average diameter in the range 0.1 $\mu$m to 150 $\mu$m (1 $\mu$m=$10^{31\ 6}$ m), preferably in the range 5 $\mu$m to 110 $\mu$m and more preferably in the range 5 $\mu$m to 80 $\mu$m, and being such that before impregnation with the active phase, the support has a total pore volume in the range 0.5 $cm^3$/g to 6 $cm^3$/g, preferably in the range 0.6 $cm^3$/g to 6 $cm^3$/g and more preferably in the range 1.5 $cm^3$/g to 6 $cm^{3/}$g. The catalyst preferably comprises a porous organic or inorganic support and at least one active phase comprising fluorosulphonic acid $FSO_3H$ or trifluoromethanesulphonic acid $CF_3SO_3H$, and at least one weakly basic aprotic organic solvent. More preferably, the catalyst comprises a porous organic or inorganic support and at least one active phase comprising trifluoromethanesulphonic acid $CF_3SO_3H$ and at least one weakly basic aprotic organic solvent.

When the support is silica, it may contain impurities such as oxides, alkalis, alkaline-earths, aluminium compounds or any other impurity known to the skilled person. The total quantity of impurities generally does not exceed 2% by weight with respect to the silica.

The porous organic or inorganic support, preferably silica, is generally such that its specific surface area is in the range 0.1 $m^2$/g to 1500 $m^2$/g before impregnation with the acid phase.

The catalyst comprises a porous organic or inorganic support and at least one active phase, impregnated into the support, comprising at least one acid selected from acids with formula R—$SO_3$H, where R is fluorine or an alkyl group or a fluorinated alkyl group (partially or completely fluorinated), R preferably being F or $CF_3$, more preferably $CF_3$, and at least one weakly basic aprotic solvent. The active phase generally comprises (in weight %) between 10% and 99% by weight, preferably between 30% and 99% by weight, more preferably between 40% and 99% of acid, and between 1% and 90%, preferably between 1% and 70%, and more preferably between 1% and 60% by weight, of the weakly basic aprotic organic solvent.

The strength of the acid used is generally in the range 95% to 100% by weight, preferably in the range 98% to 100% by weight, the complement to 100% normally being constituted by water.

The solvent used is a weakly basic aprotic organic solvent. It is generally miscible with the acid and non-miscible with the hydrocarbon phase. The basicity of the solvent must be as weak as possible in order not to reduce the protonic activity of the acid with which it is mixed. The solvent is generally selected from the group formed by sulpholane, the trade name of tetrahydrothiophene dioxide, dimethylsulphoxide (also called dimethylsulphinone), nitromethane and dioxanes (1,2-dioxane and 1,4-dioxane). Preferably, the solvent is selected from the group formed by sulpholane, dioxanes and dimethylsulphoxide. More preferably the solvent is sulpholane.

One advantage of the catalyst used in accordance with the invention over 97% to 99% strength sulphuric acid which is currently used in alkylation units is that it has an equal or higher acidity and a far lower oxidising character, since the acid comprised in the catalyst has a far lower oxidising character than sulphuric acid. A further advantage of the catalyst used in accordance with the invention over trifluoromethanesulphonic acid is a limit to the undesirable passage into hydrocarbon solution of the acid in the catalyst in the form of compounds known as alkyl triflates when the acid is trifluoromethanesulphonic acid.

A still further advantage of the catalyst used in accordance with the invention is the quality of the alkylate obtained, which has a lower sulphur content than when sulphuric acid or trifluoromethanesulphonic acid is used.

A yet still further advantage of the catalyst used in accordance with the present invention is that the use of this catalyst leads to a reduction in catalyst consumption and thus to a reduction in the operating costs of alkylation units.

The active phase generally occupies between 80% and 100% of the total pore volume of the support, preferably between 90% and 100% of the pore volume.

The preparation process for the catalyst of the invention generally comprises at least two steps. In a first step, the porous organic or inorganic support is calcined at a temperature of more than 50° C., preferably more than 80° C., more preferably in the range 150° C. to 600° C., for example at about 500° C. The duration of this calcining step is normally in the range 10 minutes to 50 hours, preferably in the range 15 minutes to 25 hours. Calcining is generally carried out in the presence of dry air or a dry air/nitrogen mixture, at a flow rate in the range 0.001 to 10 l/h/g, preferably in the range 0.1 to 5 l/h/g. The second step consists of impregnating the calcined support with the active phase. The second step can be effected using any technique which is known to the skilled person. A supplemental step for the preparation of the active phase prior to the impregnation step is generally added to the preparation process.

The invention also concerns the use of the catalyst for the catalytic alkylation of at least one isoparaffin selected from the group formed by isobutane and isopentane (i.e., isobutane and/or isopentane: isobutane, or isopentane, or isobutane and isopentane) in the presence of at least one olefin containing 3 to 6 carbon atoms per molecule.

The catalyst of the present invention is employed in a process which effects the alkylation of an isoparffin with at least one olefin under optimum conditions. In particular, since the reaction is highly exothermic (about 83.6 kJ/mol of butene transformed if the olefin is butene and the isoparaffin is isobutane), using the catalyst in accordance with the present invention can achieve good homogeneity of temperature and reactant concentration.

The operating conditions employed in the isoparaffin alkylation process using the catalyst of the present invention, more particularly the temperature and pressure, are generally selected so that the mixture, constituted by the isoparffin, olefin(s) and the reaction products, is liquid. Further, it is important that the catalyst is immersed in the liquid to ensure good liquid-solid contact.

The catalyst of the invention is advantageously employed in the reaction zone where the isobutane and/or isopentane is alkylated with at least one olefin containing 3 to 6 carbon atoms per molecule, in the liquid phase and mixed with the isoparaffin and/or a mixture of isoparaffins. The catalyst of the invention can be used in an expanded bed, in a near perfectly mixed reaction zone or in a circulating bed. Preferably, it is employed in a process which uses a continuous liquid phase, the catalyst being used in the form of a suspension using one of the two preferred procedures described below.

A first preferred implementation for the catalyst of the invention uses a near perfectly mixed reaction zone, i.e., a perfect mixture or a near perfect mixture(stirred or Grignard tank), using at least one stirring means, for example at least one screw, to obtain sufficient stirring of the catalyst suspended in the liquid hydrocarbon phase, the phase generally comprising the isoparffin (isobutane and/or isopentane), at least one olefin, possibly at least one inert diluent (for example propane and normal butane) and the alkylation reaction products. The feed to be converted, constituted by isobutane and/or isopentane and at least one olefin, can for example be introduced as a liquid at at least one point in the liquid hydrocarbon phase present in the reaction zone.

A second preferred implementation for the catalyst of the present invention in suspension in a hydrocarbon phase is a co-current mobile bed, i.e., a circulating bed. In this implementation, the catalyst suspended in the liquid hydrocarbon phase, which latter generally comprises the isoparaffin (isobutane and/or isopentane), at least one olefin, possibly at least one inert diluent (for example propane or normal butane) and the alkylation reaction products, circulates from bottom to top in the reaction zone. The ensemble constituted by the catalyst suspended in the hydrocarbon phase then circulates through at least one heat exchanger and at least one pump before being reintroduced to the inlet to the reaction zone. The feed to be converted, constituted by the isobutane and/or isopentane and at least one olefin, is introduced either as a liquid or as a gas at at least one point in the reaction zone.

In the two implementations described above, the isoparaffin (isobutane and/or isopentane) which is unconverted or has been introduced in excess with respect to the reaction stoichiometry is generally recycled after separation of the alkylate, either by direct introduction into the reaction zone, or by mixing with the feed to be converted.

The isoparaffin-olefin mixture is generally introduced into the reaction zone at an hourly space velocity, expressed as the weight of olefin introduced per unit weight of catalyst per hour (wwh), in the range 0.001 $h^{-1}$ to 10 $h^{-1}$, preferably in the range 0.002 $h^{-1}$ to 2 $h^{-1}$. The mixture can also be formed inside the reaction zone. In all cases, the mixture produced is in the reaction zone under temperature and pressure conditions which ensure that the hydrocarbon mixture remains liquid on the catalyst.

The reaction temperature is generally below +40° C., preferably below +15° C. and more preferably in the range +5° C. to −5° C. The pressure in the reaction zone is sufficient to maintain the hydrocarbons in the liquid state in that zone.

In order to limit secondary reactions, an excess of isoparaffin(s) with respect to olefin(s) can be used. As an example, in the case of alkylation of isobutane with a butene, the isobutane can be introduced pure into the feed or as a mixture of butanes containing, for example, at least 40% of isobutane. Further, a butene can be introduced pure or as a mixture of butene isomers. In all cases, the isobutane/butene molar ratio in the feed is generally in the range 1 to 100, preferably in the range 3 to 50 and more preferably in the range 5 to 15.

When the nature of the catalyst and the reaction conditions are carefully selected (in particular the temperature), the catalyst of the invention can produce alkylation products of at least one isoparaffin and at least one olefin which are important as motor fuels and petrol constituents and which comprise, for example, at least 60 mole % of paraffins containing 8 carbon atoms per molecule and less than 1 mole % of unsaturated compounds, the paraffins containing 8 carbon atoms per molecule comprising 70 to 98 mole % of trimethylpentanes.

A further advantage of the catalyst of the present invention is the possibility of alkylating, at low temperature, isobutane with mixtures of olefins containing 3 to 6 carbon atoms per molecule, where the proportion of olefins containing more than 4 carbon atoms per molecule is very high.

The following examples illustrate the invention without in any way limiting its scope.

EXAMPLE 1

Preparation of catalyst 1 in accordance with the invention 100 g of an active phase in accordance with the invention was prepared by mixing 80 g of 98% strength trifluoromethanesulphonic acid with 20 g of sulpholane which had been vacuum distilled. The prepared acid phase thus contained 20% by weight of sulpholane and 80% by weight of 98% strength trifluoromethanesulphonic acid.

10 g of silica with a specific surface area of 383 $m^2/g$, a total pore volume of 2.6 $cm^3/g$ and an average particle diameter of 35 $\mu m$ was activated by calcining in dry air for 4 hours at 500° C. The activated silica was stored under argon. 6.5 g of the silica was then dry impregnated, in the absence of moisture, with 26.5 g of the active phase prepared using the procedure described above.

The solid obtained, catalyst 1, contained 80.3% by weight of active phase.

Alkylation of isobutane with 2-butene using catalyst 1

Catalyst 1 was used to alkylate isobutane with 2-butene to produce branched paraffins with high octane numbers. 33 g of catalyst 1 as prepared above was introduced into a 360 ml volume Fischer & Porter type reactor which had been purged with a stream of argon. The reactor containing the catalyst was then closed, placed under low vacuum, then cooled to a temperature of −10° C.

200 ml of isobutane was added to the reactor containing the catalyst, with stirring, the reactor being immersed in a cold bath at −4° C. The system (catalyst+isobutane) was stirred for 30 minutes to homogenise the temperature.

17.8 g of 2-butene was then added continuously and regularly over a total period of 5 hours, the reactor temperature being held at −1° C. for the entire injection period.

After reaction, the hydrocarbon phase (alkylate+isobutane) was extracted from the reactor then analysed by gas chromatography. Its composition by weight is shown in Table 1. 100% of the olefin was converted.

EXAMPLE 2

Preparation of comparative catalyst 2

In this example, 98 weight % strength trifluoromethanesulphonic acid was used with no additions.

10 g of silica with a specific surface area of 383 $m^2/g$, a total pore volume of 2.6 $cm^3/g$ and an average particle diameter of 35 $\mu m$ was activated by calcining in dry air for 4 hours at 500° C. The activated silica was stored under argon. 6.5 g of the silica was then dry impregnated, in the absence of moisture, with 26.5 g of the active phase prepared using the procedure described above.

The solid obtained, catalyst 2, contained 80.3% by weight of active phase.

Alkylation of isobutane with 2-butene using catalyst 2

Catalyst 2 was tested under the same operating conditions as those described for Example 1. The catalytic results obtained are shown in Table 1. 100% of the olefin was converted.

TABLE 1

| | CATALYST 1 (invention) | CATALYST 2 (comparative) |
|---|---|---|
| $C_5$–$C_7$ | 2.7 | 1.7 |
| $C_8$ total | 94.5 | 85.8 |
| $C_9$ | 2.8 | 12.5 |

Table 1 shows the positive effect of the presence of a weakly basic aprotic organic solvent in the active phase comprising trifluoromethanesulphonic acid, the solvent in this case being sulpholane. For identical operating conditions, catalyst 1 had a higher selectivity for $C_8$ compounds and a lower selectivity for the undesirable heavy $C_9^+$ compounds.

EXAMPLE 3

Preparation of catalyst 3 in accordance with the invention 10 g of silica with a total pore volume of 2.6 $cm^3/g$, a specific surface area of 402 $m^2/g$, and an average particle diameter of 76 $\mu m$ was activated by drying for 12 hours at 150° C. The activated silica was stored under nitrogen. 6.2 g of the silica was then dry impregnated with 25.2 g of the active phase prepared in Example 1.

The solid obtained, catalyst 3, contained 80.25% by weight of active phase. It was stored under argon in the absence of moisture.

Alkylation of isobutane with 2-butene using catalyst 3

31.4 g of catalyst 3 prepared using the method described above was introduced into a 360 ml volume Fischer & Porter type reactor which had been purged with a stream of argon. The reactor containing the catalyst was then closed, placed under low vacuum, then cooled to a temperature of −10° C.

200 ml of isobutane was added to the reactor containing the catalyst, with stirring (screw), the reactor being immersed in a cold bath at −4° C. The system (catalyst 3+isobutane) was stirred for 30 minutes to homogenise the temperature.

15.6 g per hour of 2-butene was regularly added over a total period of 5 hours, the reactor temperature being held at −1° C. for the entire injection period.

After reaction, the hydrocarbon phase (alkylate+isobutane) was extracted from the reactor then analysed by gas chromatography. Its composition by weight is shown in Table 2. 100% of the olefin was converted.

EXAMPLE 4

Preparation of comparative catalyst 4

10 g of the same silica as that used in Example 3 was prepared in identical fashion to that employed in Example 3. 6.2 g of the silica was then dry impregnated with 25.2 g of the acid used in Example 2.

The solid obtained, catalyst 4, contained 80.25% by weight of acid phase. It was stored under argon in the absence of moisture.

Alkylation of isobutane with 2-butene using catalyst 4

31.4 g of catalyst 4 prepared using the method described above was introduced into a 360 ml volume Fischer & Porter type reactor which had been purged with a stream of argon. The reactor containing the catalyst was then closed, placed under low vacuum, then cooled to a temperature of −10° C. 200 ml of isobutane was then added to the reactor containing the catalyst, with stirring (screw), the reactor being immersed in a cold bath at −4° C. The system (catalyst 4+isobutane) was stirred for 30 minutes to homogenise the temperature.

15.6 g per hour of 2-butene was regularly added over a total period of 5 hours, the reactor temperature being held at −1° C. for the entire injection period.

After reaction, the hydrocarbon phase was extracted from the reactor, the isobutane was slowly evaporated off and the alkylate was recovered and analysed by gas chromatography. Its composition by weight is shown in Table 2. 100% of the olefin was converted.

TABLE 2

| | CATALYST 3 (invention) | CATALYST 4 (comparative) |
|---|---|---|
| $C_5$–$C_7$ | 3.3 | 3.9 |
| $C_8$ total | 92.1 | 82.2 |
| $C_9$ | 4.6 | 13.9 |

Table 2 shows the positive effect of the presence of a weakly basic aprotic organic solvent in the active phase comprising trifluoromethanesulphonic acid, the solvent in this case being sulpholane. For identical operating conditions, catalyst 3 had a higher selectivity for $C_8$ compounds and a lower selectivity for the undesirable heavy $C_9^+$ compounds.

EXAMPLE 5

Preparation of catalyst 5 in accordance with the invention 50 g of an active phase in accordance with the invention was prepared by mixing 40 g of 100% strength trifluoromethanesulphonic acid with 10 g of sulpholane which had been vacuum distilled. The 40 g of 100% strength trifluoromethanesulphonic acid had been obtained by mixing 30.45 g of 98% strength trifluoromethanesulphonic and 9.55 g of trifluoromethanesulphonic anhydride $(CF_3SO_2)_2O$. The prepared acid phase thus contained 20% by weight of sulpholane and 80% by weight of 100% trifluoromethanesulphonic acid.

10 g of the same silica as that used in Example 3 was then prepared in identical fashion to the method employed in Example 3. 6.5 g of the silica was dry impregnated with 26.1 g of the active phase prepared using the procedure described above.

The solid obtained, catalyst 5, contained 80.1% by weight of active phase. It was stored under argon in the absence of moisture.

Alkylation of isobutane with 2-butene using catalyst 5

32.6 g of catalyst 5 as prepared above was introduced into a 360 ml volume Fischer & Porter type reactor which had been purged with a stream of argon. The reactor containing the catalyst was closed, placed under low vacuum, then cooled to a temperature of −10° C.

200 ml of isobutane was then added to the reactor containing the catalyst, with stirring (screw), the reactor being immersed in a cold bath at −4° C. The system (catalyst 5+isobutane) was stirred for 30 minutes to homogenise the temperature.

19.6 g per hour of 2-butene was regularly added over a total period of 5 hours, the reactor temperature being held at −1° C. for the entire injection period.

After reaction, the hydrocarbon phase (alkylate+isobutane) was extracted from the reactor then analysed by gas chromatography. Its composition by weight is shown in Table 3. 100% of the olefin was converted

EXAMPLE 6

Preparation of comparative catalyst 6

50 g of 100% strength trifluoromethanesulphonic acid was obtained by mixing 38.06 g of 98 weight % strength trifluoromethanesulphonic acid and 11.94 g of trifluoromethanesulphonic acid anhydride $(CF_3SO_2)_2O$. The acid phase thus contained 100 % of 100 weight % strength trifluoromethanesulphonic acid $(CF_3SO_3H)$.

10 g of the same silica as that used in Examples 3 and 5 was then prepared using the same method as that employed in Example 3. 6.5 g of the silica was then dry impregnated with 26.1 g of the active phase prepared using the procedure described above.

The solid obtained, catalyst 6, contained 80.1% by weight of active phase. It was stored under argon in the absence of moisture.

Alkylation of isobutane with 2-butene using catalyst 6

32.6 g of catalyst 6 as prepared above was introduced into a 360 ml volume Fischer & Porter type reactor which had been purged with a stream of argon. The reactor containing the catalyst was closed, placed under low vacuum, then cooled to a temperature of −10° C.

200 ml of isobutane was added to the reactor containing the catalyst, with stirring (screw), the reactor being immersed in a cold bath at −4° C. The system (catalyst 6+isobutane) was stirred for 30 minutes to homogenise the temperature.

19.6 g per hour of 2-butene was regularly added over a total period of 5 hours, the reactor temperature being held at −1° C. for the entire injection period.

After reaction, the hydrocarbon phase (alkylate+isobutane) was extracted from the reactor then analysed by gas chromatography. Its composition by weight is shown in Table 3. 100% of the olefin was converted.

TABLE 3

| | CATALYST 5 (invention) | CATALYST 6 (comparative) |
|---|---|---|
| $C_5$–$C_7$ | 2.5 | 4.8 |
| $C_8$ total | 94.2 | 81.9 |
| $C_9$ | 3.3 | 13.3 |

Table 3 shows the positive effect of the presence of a weakly basic aprotic organic solvent in the active phase comprising trifluoromethanesulphonic acid, the solvent in this case being sulpholane. For identical operating conditions, catalyst 5 had a higher selectivity for $C_8$ compounds and a lower selectivity for the undesirable heavy $C_9^+$ compounds.

We claim:

1. A catalyst comprising a porous organic or inorganic support and at least one active phase comprising at least one acid of the formula $RSO_3H$, where R is fluorine or fluroinated alkyl group, and at least one weakly basic aprotic organic solvent selected from the group consisting of sulpholane, dimethylsulphoxide, nitromethane and dioxanes, said support having been impregnated with the active phase, said catalyst being essentially constituted by particles with an average diameter in the range of 0.1 $\mu$m to 150 $\mu$m, and being such that before impregnation with the active phase, said support has a total pore volume in the range 0.5 $cm^3$/g to 6 $cm^3$/g.

2. A catalyst according to claim 1, in which the active phase comprises 30% to 99% by weight of acid and 1% to 70% by weight of solvent, and in which the acid has a strength of 95% to 100%.

3. A catalyst according to claim 2 in which the active phase comprises 40% to 99% by weight of acid and 10% to 60% by weight of solvents, and in which the acid is of the strength of 98% to 100%.

4. A catalyst to claim 1, in which the acid is fluorosulphonic acid or trifluoromethanesulphonic acid.

5. A catalyst according to claim 1, in which the acid is trifluoromethansesulphonic acid.

6. A catalyst according to claim 5, wherein the solvent is dimethylsulphoxide.

7. A catalyst according to claim 1 in which said support is silica.

8. A process of catalytic alkylation comprising contacting catalyst according to claim 1 in a reaction zone with (a) at least one isoparaffin selected from the group consisting of isobutane and isopentane, and (b) with at least one olefin containing 3 to 6 carbon atoms per molecule, in which the reaction temperature is below +40° C. and the pressure in the reaction zone is sufficient to maintain the hydrocarbons in the liquid state in said zone.

9. A process according to claim 8, in which the catalyst is used in a near perfectly mixed reaction zone.

10. A process according to claim 8, in which the catalyst is used in a co-current mobile bed.

11. A catalyst comprising a porous organic or inorganic support and at least one active phase comprising at least one acid of the formula $R—SO_3H$, where R is fluorine or a fluorinated alkyl group, and at least one weakly basic aprotic organic solvent, selected from the group consisting of sulpholate, dimethylsulphoxide, and dioxanes, said support having been impregnated with the active phase, said catalyst being essentially constituted by particles with an average diameter in the range 0.1 $\mu$m, to 150 $\mu$m, and being such that before impregnation with the active phase, said support has a total pore volume in the range 0.5 $cm^3$/g to 6 $cm/^3$g.

12. A catalyst according to claim 11, in which the solvent is sulpholane.

13. A catalyst according to claim 12, in which the acid is trifluoromethanesulphonic acid.

14. A catalyst according to claim 13, in which said support is silica.

15. A catalyst according to claim 11, in which the acid is fluorosulphonic acid or trifluoromethanesulphonic acid.

16. A catalyst according to claim 15, wherein said solvent is dimethylsulphoxide.

17. A process of catalytic alkylation comprising contacting the catalyst according to claim 11 in a reaction zone with (a) at least one isoparaffin selected from the group consisting of isobutane and isopentane, and (b) with at least one olefin containing 3 to 6 carbon atoms per molecule, in which the reaction temperature is below +40° C. and the pressure in the reaction zone is sufficient to maintain the hydrocarbons in the liquid state in said zone.

18. A process according to claim 17, wherein the solvent in the active phase of the catalyst is sulpholane.

19. A process according to claim 17, in which the acid in the active phase of the catalyst is trifluoromethanesulphonic acid.

20. A process according to claim 17, in which the catalyst is used in a near perfectly mixed reaction zone.

21. A process according to claim 17, in which the catalyst is used in a co-current mobile bed.

22. A catalyst consisting essentially of a porous organic or inorganic support and at least one active phase consisting essentially of at least one acid of the formula $R—SO_3H$, where R is fluorine or a fluorinated alkyl group, and at least one weakly basic aprotic organic solvent selected from the group consisting of sulpholane, dimethylsulphoxide, and dioxanes, said support having been impregnated with the active phase, said catalyst being essentially constituted by particles with an average diameter in the range 0.1 $\mu$m to 150 $\mu$m, and being such that before impregnation with the active phase, said support has a total pore volume in the range 0.5 $cm^3$/g to 6 $cm/^3$ g.

* * * * *